United States Patent
Gajic et al.

(10) Patent No.: US 8,527,449 B2
(45) Date of Patent: Sep. 3, 2013

(54) SEPSIS MONITORING AND CONTROL

(75) Inventors: Ognjen Gajic, Rochester, MN (US); Vitaly Herasevich, Marshfield, WI (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 250 days.

(21) Appl. No.: 12/940,729

(22) Filed: Nov. 5, 2010

(65) Prior Publication Data

US 2011/0137852 A1 Jun. 9, 2011

Related U.S. Application Data

(60) Provisional application No. 61/258,450, filed on Nov. 5, 2009.

(51) Int. Cl.
*G06N 5/02* (2006.01)
(52) U.S. Cl.
USPC .............................................. 706/54; 600/301
(58) Field of Classification Search
None
See application file for complete search history.

(56) References Cited

U.S. PATENT DOCUMENTS

| | | | |
|---|---|---|---|
| 5,942,986 A * | 8/1999 | Shabot et al. | 340/7.29 |
| 2003/0181815 A1 * | 9/2003 | Ebner et al. | 600/483 |
| 2005/0125256 A1 | 6/2005 | Schoenberg et al. | |
| 2006/0271408 A1 * | 11/2006 | Rosenfeld et al. | 705/3 |
| 2008/0091088 A1 * | 4/2008 | Kiani | 600/301 |
| 2008/0208618 A1 * | 8/2008 | Schoenberg et al. | 705/2 |

OTHER PUBLICATIONS

Shortliffe E. et al., "Biomedical Informatics. Computer Applications in Health Care and Biomedicine", 3rd Ed., Springer, 2006.*
Kogure Y. et al., "The Applications of Remote Patient Monitoring System using a Java-enabled 3G Mobile Phone", IFMBE Proceedings, pp. 3658-3661, 2007.*
Herasevich V. et al., "ICU of the future: informatics infrastructure for syndrome surveillance, decision support, data mining, and modeling of critical illness", Journal of Critical care, vol. 22, Issue 4, p. 340, Dec. 2007.*
Herasevich V. et al., "Rule base system for identification of patients with specific critical care syndromes: The sniffer for acute lung injury", AMIA Symposium Proceedings, p. 972, Oct. 2007.*
Herasevich V. et al., "Designing and testing computer based screening engine for severe sepsis/septic shock", AMIA Symposium Proceedings, p. 966, Nov. 2008.*

(Continued)

*Primary Examiner* — Jeffrey A Gaffin
*Assistant Examiner* — Dave Misir
(74) *Attorney, Agent, or Firm* — Fish & Richardson P.C.

(57) ABSTRACT

A computer-implemented sepsis alerting method is disclosed. The method involves automatically extracting with a computer system, from records maintained for a patient under care in a healthcare facility, information from a electronic medical record, and obtaining with the computer system information about real-time status of the patient. The method also involves using the information from the electronic medical record and the information about the real-time status to determine whether the patient is likely to be suffering from dangerous probability of sepsis, using information from the electronic medical record to determine whether treatment for sepsis is already being provided to the patient, and electronically alerting a caregiver over a network if it is determined that a potentially dangerous level of sepsis exists and that treatment for sepsis is not already being provided.

17 Claims, 5 Drawing Sheets

(56) References Cited

OTHER PUBLICATIONS

Thompson D. et al., "Sepsis Alert and Diagnostic System. Integrating Clinical Systems to Enhance Study Coordinator Efficiency", CIN, vol. 21, No. 1, pp. 22-26, Jan./Feb. 2003.*

Dunsmuir D. et al., "A Knowledge Authoring Tool For Clinical Decision Support", Journal of Clinical Monitoring and Computing, pp. 189-198, 2008.*

* cited by examiner

SEPSIS MONITORING AND CONTROL

CROSS-REFERENCE TO RELATED APPLICATION

This application claims priority to U.S. Provisional Application Ser. No. 61/258,450, filed on Nov. 5, 2009, entitled "Sepsis Monitoring and Control," the entire contents of which are hereby incorporated by reference.

STATEMENTS AS TO FEDERALLY SPONSORED RESEARCH

This invention was made with government support under grant number RR024151 awarded by the National Center for Research Resources. The government has certain rights in the invention.

TECHNICAL FIELD

This document relates to computer-based systems and techniques for monitoring a human patient for complex physiological syndromes such as sepsis and sepsis shock.

BACKGROUND

Septic shock is one of several inflammatory states (along with sepsis and severe sepsis) that result from a person's systemic response to bacterial infection. In severe cases, tissue perfusion may be greatly reduced, and a patient may develop shaking chills, fever, hypotension, oliguria, and confusion. Ultimately, sepsis can cause acute failure of multiple organs (e.g., lungs, kidneys, and liver), potentially causing death. Septic conditions are generally treated by aggressive fluid resuscitation, antibiotics, surgical excision of infected or necrotic tissues and drainage of pus, supportive care, and sometimes intensive control of blood glucose and administration of corticosteroids and activated protein C. Generally, patients suffering severe sepsis are provided for in an Intensive Care Unit (ICU) of a hospital.

When in an ICU, a patient may be provided for by a variety of equipment such as IV drips and drug delivery mechanisms, bed-side monitors, and the like. In addition, ICU patients are generally continuously monitored for a number of physiological factors, including pulse rate, respiratory rate, and blood pressure. Periodic tests are also performed on such a patient to obtain updated indications of the patient's current physiological status.

SUMMARY

This document describes systems and techniques that may be used to monitor and detect sepsis (which, as used here, can include severe sepsis and septic shock), and detect sepsis treatment that may be performed on a patient so as to notify caregivers of failures to treat the patient in a timely manner. For example, if the system fails to detect timely, evidence-based interventions within an Electronic Medical Record (EMR), it may provide notifications in the form of an early warning clinical alert, such as a page or text message, including messages that require proof of a response from the notified caregiver. Such an alert may be in addition to an initial alert provided to a caregiver when the system initially notices that the patient is exhibiting symptoms of sepsis. The subsequent alert may be provided to a different caregiver than the initial alert, to help ensure that follow-up care will be provided.

In certain implementations, such systems and technique may provide one or more advantages. For example, patient care and safety may be improved when a system can monitor the patient automatically, and can combine data from multiple sources, including real-time monitoring of patient-connected equipment and extraction of data from electronic medical records. Also, where the monitoring system is connected to a communication system, a caregiver can be alerted and can address any dangerous situations that may arise. The alerts may be made judiciously also, so that a caregiver will understand that the alerts are important when they are given. Moreover, the presence or absence of treatment for such conditions can be identified by separately checking subsequent actions that have been recorded in an EMR after the time of an initial alert, in addition to continued monitoring of a patient by the system (to determine whether the patient's condition is, in fact, improving). In this manner, patients who are suffering from sepsis may obtain quick intervention and treatment, which can be lifesaving in some situations.

In one implementation, a computer-implemented sepsis alerting method is disclosed. The method comprises automatically extracting with a computer system, from records maintained for a patient under care in a healthcare facility, information from a electronic medical record; obtaining with the computer system information about real-time status of the patient; using the information from the electronic medical record and the information about the real-time status to determine whether the patient is likely to be suffering from dangerous probability of sepsis; using information from the electronic medical record to determine whether treatment for sepsis is already being provided to the patient; and electronically alerting a caregiver over a network if it is determined that a potentially dangerous level of sepsis exists and that treatment for sepsis is not already being provided. The method can also include electronically automatically monitoring with the computer system the patient's electronic medical record to determine whether intervention has occurred to treat the potentially dangerous level of sepsis; and providing follow-up electronic alerts if a determination is made that intervention has not occurred.

In some aspects, obtaining real-time status of the patient comprises querying, with the computer system, a bed-side monitor for the patient or a controller to which the bed-side monitor reports information about the patient. Also, determining whether the patient is likely to be suffering from sepsis can comprise applying predetermined rules to values of patient parameters obtained with the computer system. The values can include values for patient heart rate, respiration rate, and blood pressure; values generated by a blood test on the patient's blood; and values that include keywords in notes in an electronic medical record for the patient. Machine-readable tangible media storing instructions for performing the above methods may also be provided.

In another implementation, a computer-implemented system to monitor and report on patient condition is disclosed. The system comprises a computer system that implements a data extractor to automatically extract, from records maintained for a patient under care in a healthcare facility, information from a electronic medical record and obtain information about real-time status of the patient. The system also comprises a patient evaluator programmed to using extracted by the data extractor to determine whether the patient is likely to be suffering from dangerous probability of sepsis. In addition, the system comprises a contact management system arranged to electronically alert a caregiver over a network if the patient evaluator determines that a potentially dangerous level of sepsis exists. In certain aspects, the system can also include an alerting system to automatically monitor the patient's electronic medical record to determine whether intervention has occurred to treat the potentially dangerous level of sepsis and to initiate follow-up electronic alerts if a determination is made that intervention has not occurred.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document describes systems and techniques for identifying problematic physiological conditions for a patient who may be suffering from sepsis. The systems and techniques take into account real-time data from equipment that is currently connected to the patient and other patient test data from external sources, which are sources that are not measuring a current (or near current) patient status. Such external sources may store electronic data that has been reported from a hospital laboratory on tests that have previously been performed on the patient, the patient's blood or tissue, or a similar source. The data that is accessed by the systems may be analyzed in a predetermined manner and according to established rules to determine whether the patient is suffering from sepsis.

When such a positive determination is made, the systems may automatically notify an appropriate caregiver. One mechanism for notification may include identifying a caregiver of an appropriate type (e.g., a physician or a particular specialist physician) and then identifying a particular caregiver (e.g., a physician who is currently on call). Contact information for the particular caregiver may then be accessed and an alerting message may be sent to the caregiver. The message may include a page or an automated telephone call. The message may also include a text message or email message. The message may also include information about the patient and the patient's status (e.g., the message may list the patient's current vital signs). Alternatively, or in addition, the message may include a mechanism, such as a selectable hyperlink, to permit the recipient caregiver to access additional information about the patient's condition. For example, the hyperlink may lead to an EMR or report from an EMR for the patient, so that the caregiver can quickly see all information that might be relevant for them to determine the best course of care for the patient.

The initial alert may also be blocked upon the system determining that appropriate treatment is already being provided to the patient. For example, upon identifying that the patient may be suffering from sepsis, the system may check the patient's EMR to identify whether actions directed to treating sepsis have been taken by caregivers recently. For example, the system may check the EMR to determine whether a caregiver has notified a sepsis team, whether a caregiver has placed a central line, or has ordered another treatment that indicates that sepsis or symptoms of sepsis are already being addressed for the patient.

Because sepsis can be a very serious condition, the system may also make efforts to determine objectively whether the patient has been properly treated for the condition that raised an alert of sepsis, after an alert is delivered. For example, the system may continue to monitor the patient's condition to determine whether it has improved. The system may also periodically check the patient's EMR to determine whether a caregiver has entered a note to indicate that they took an appropriate follow-up action on the patient, such as by increasing fluids or antibiotics to the patient, and the other actions noted in the prior paragraph.

Figure 1:
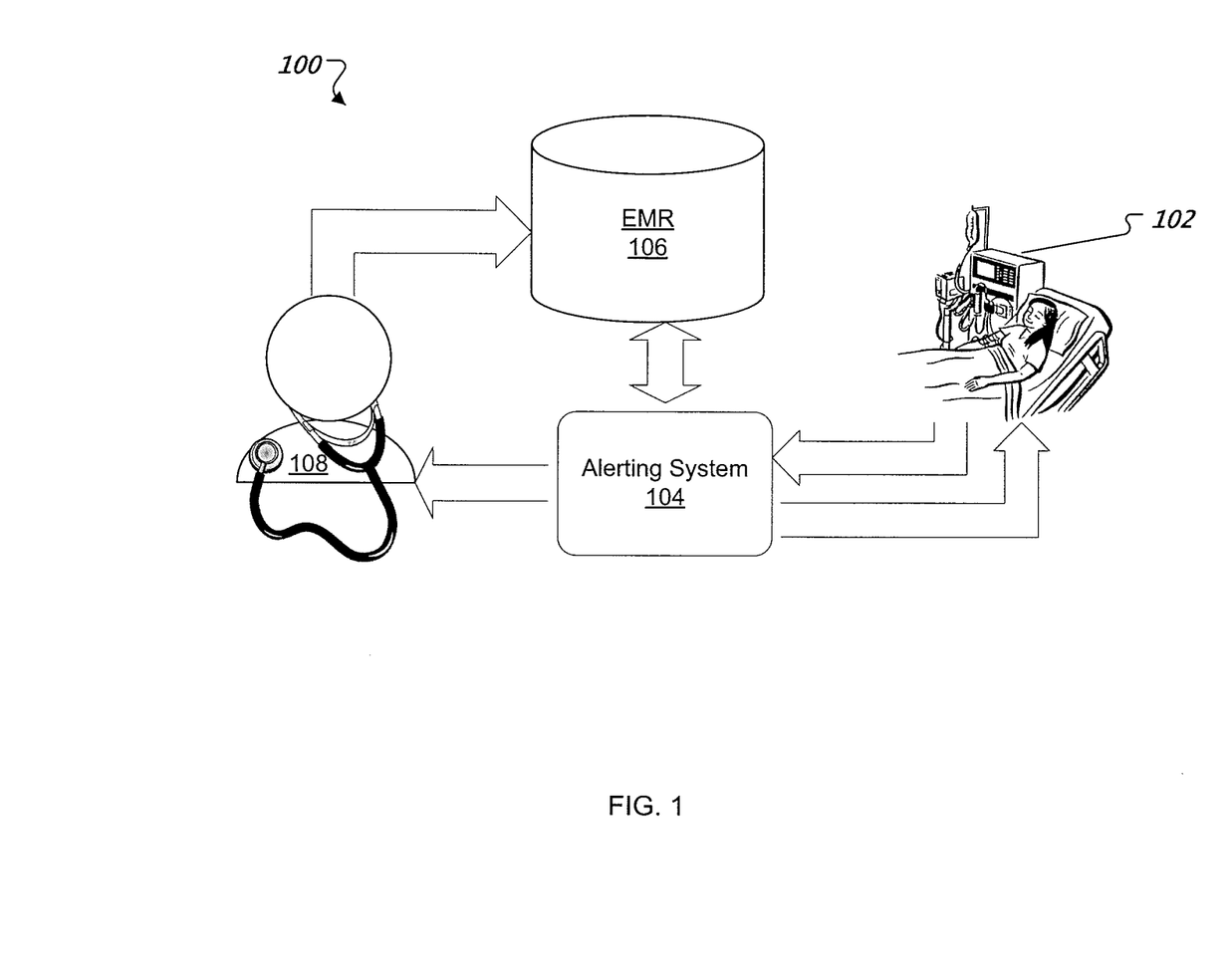
FIG. 1 is a conceptual flow diagram showing the processing of patient related information into a clinical decision in aid of the patient.

FIG. 1 is a conceptual flow diagram showing the processing of patient related information into a clinical decision in aid of the patient. In the figure, a patient information system 100 is shown as providing information about a patient to a caregiver 108. The patient is connected to a bed-side monitor 102 and thus may be an ICU patient in relatively serious condition. The bed-side monitor 102 includes electronic components for measuring parameters of the patient in real-time and turning those parameters into machine- and/or human-discernable variables. For example, light propagation through a relatively thin portion of a patient's anatomy (e.g., a fingertip) can be measured, and a number can be generated that represents a blood oxygen level for the patient. Other monitored variables may include blood pressure, respiration rate, heart/pulse rate, and patient temperature.

Other variables may be measured non-continuously or manually and may be entered, e.g., by a caregiver such as a physician or nurse, into an EMR system in a familiar manner. Such variables may include patient temperature and blood pressure in appropriate circumstances. Yet other variables may be determined from testing of the patient's blood or tissue outside the patient's room, such as by drawing the patient's blood and providing it to a laboratory for testing. Such variables may include, among many other things, white blood cell count, lactate, base, and anion gap.

Certain of such parameters may be read by an alerting system 104 that is in electrical or other such communication with the bed-side monitor 102. The alerting system 104 may be a computer-implemented system that is programmed to gather patient-related information from multiple sources, including the controller for the bed-side monitor 102 (or from the EMR if the EMR itself obtains the information from the monitor), and to apply rules to such gathered data in order to determine whether a potentially dangerous situation exists for the patient, such as a condition that indicates that the patient may be suffering from sepsis. The alerting system 104 in this example also acquires information from an EMR system and applies the rules to that information and the other gathered information.

Such gathering of information by the alerting system may occur periodically according to a clock that is associated with the alerting system 104, or it may occur in response to a patient-related event, such as a substantial change in bed-side monitor parameters being provided to the alerting system 104 (either directly or through the EMR system 106).

The information extracted by the alerting system 104 from the EMR system 106 can take a variety of forms. For example, laboratory results can be associated with certain conditions of the patient. Also, text in medical records can be identified, parsed, and interpreted by the system 100, and can be used to match predetermined words so as to identify concepts that are being addressed by such text. Billing codes may also be analyzed to determine what activities have been taken with respect to a patient.

The alerting system 104 is shown as sending communications to a caregiver 108. The communications may take a variety of familiar forms such as pager messages in text, or standard text messages, among other possibilities. Sending of the messages may be based upon an automatic determination by the alerting system 104 that the patient may be suffering from sepsis or septic shock, and the alert may be designed to draw a corrective response from the caregiver, such as having the caregiver come to the patient's aid and administer to the patient, or to have the caregiver contact another caregiver (e.g., a shift nurse who is on duty) to provide follow-up, including care for the patient.

The caregiver 108 may read any provided messages, which, based on a determination made by the alerting system 104, will indicate that a dangerous sepsis condition may exist. The caregiver 108 may then return to the patient's room, review the bed-side monitor 102 and its parameters in more detail, and change the patient's care to ensure the patient's safety. The caregiver 108 can also call into an ICU and direct another caregiver to modify a course of treatment for the patient. For example, the patient may be provided with additional fluids, be given antibiotics, be scheduled for surgery for the excision of infected or necrotic tissues and drainage of pus, or be otherwise treated.

Also, modification of the bed-side monitor's 102 operation can be achieved by the caregiver 108 either directly or remotely, and whether automatically or manually, and is shown in the figure by an arrow leading back from the alerting system 104 to the bed-side monitor 102. For example, the alerting system 104 may determine that the bed-side monitor 102 needs to be reset or otherwise adjusted, at least until caregiver 108 can turn their attention to the bed-side monitor 102 and manually override whatever setpoint has been automatically selected. Such automatic override may be allowed only under circumstances where it has been determined that such action does not create a risk to the patient.

The provision of an initial alert may be blocked (or a different, lesser form of alert may be provided) before or after a determination has been made that the patient may have sepsis, if the system determines that the patient is already being treated for sepsis. For example, the system may analyze the patient's EMR to determine whether a sepsis team has been notified recently, whether a caregiver has placed a line for the patient or increased antibiotics for the patient, or taken other actions that are consistent with the caregiver or caregivers recognizing that the patient needs to have a sepsis condition addressed.

Another arrow is shown leading from the caregiver 108 back to the EMR system 106, to signify that when the caregiver 108 attends to the patient, the caregiver may make a note in the patient's EMR. For example, the physician may record that the patient has been provided a certain level of antibiotics that differs from the level the patient was receiving before the generation of the alert to the caregiver 108.

The two-way arrow between the EMR system 106 and the alerting system 104 indicates that the alerting system may schedule an automatic follow-up check of the patient's EMR data to determine whether appropriate follow-up by the caregiver has occurred. For example, the alerting system 104 may not simply depend on the caregiver's 108 response to an alert to assume that the patient's treatment has changed. Instead, the alerting system 104 may check the patient's EMR. Such a check may initially involve a check for all notes or other entries in the patient's EMR after the time of the alert. Those entries may then be mapped to topics, keywords, or billing codes that are known to be proper responses to the condition of the patient that originally generated the alert, which in this case could have been sepsis, severe sepsis, or the onset of septic shock. For example, the alerting system 104 may check for the presence of an entry that indicates that the patient was given additional fluids or antibiotics.

If the check of the EMR data does not plainly indicate that appropriate steps have been taken, the alert system 104 may take appropriate follow-up action, including escalating action. For example, the system 104 may alert the caregiver 108 again and request a positive response. If such a response is not adequate, the system may notify an alternative caregiver or caregivers, such as a shift nurse or a supervisory physician, until positive evidence is received that the patient has been attended to. Depending on the circumstances, an affirmative response from a caregiver, including caregiver 108, may be sufficient to cause the system 104 to wait, but at other points, evidence-based confirmation, such as in the form of entries in the EMR system, may be required (at least to avoid elevating the situation to another caregiver).

Figure 2A:
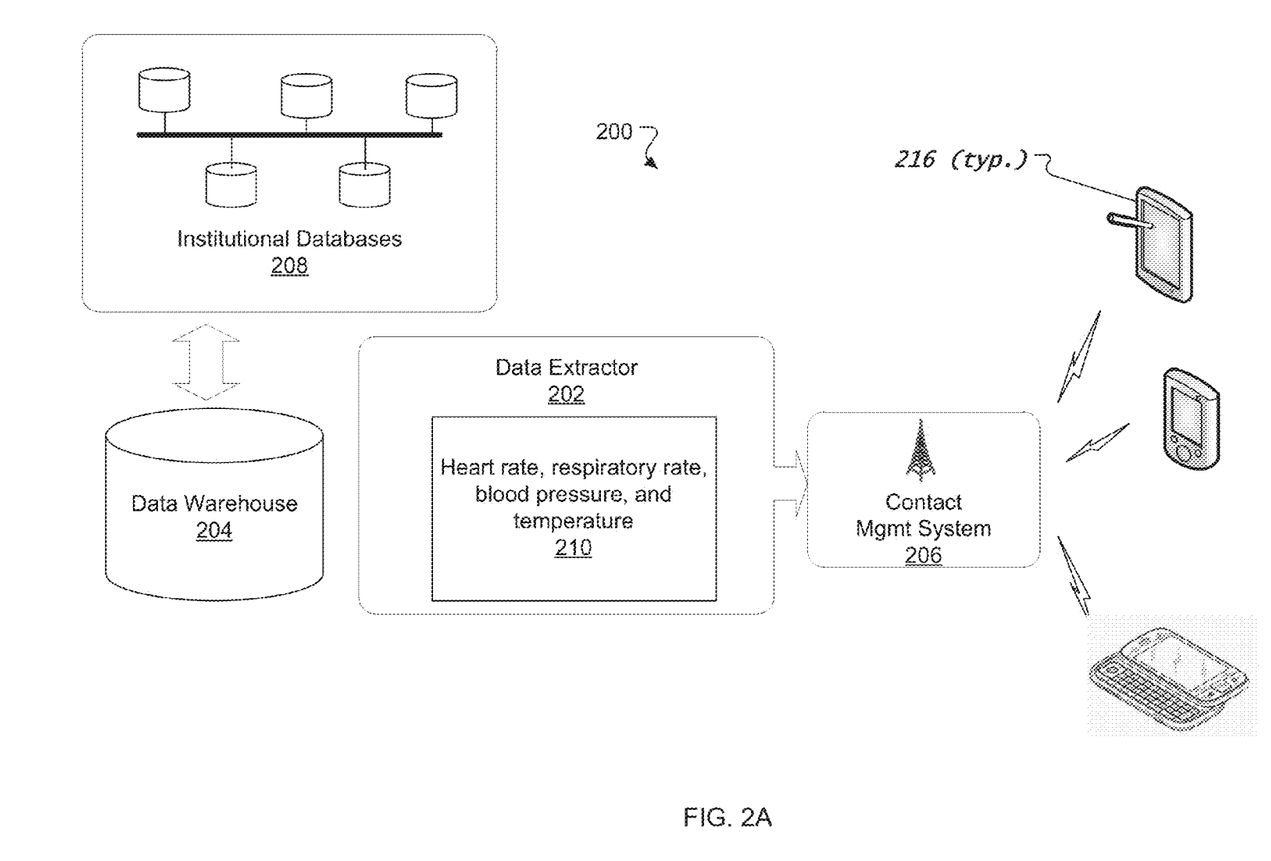
FIG. 2A is a block diagram showing processing of various patient-related data in order to generate an alert for a caregiver.

FIG. 2A is a block diagram showing processing of various patient-related data in order to generate an alert for a caregiver. Such processing occurs by use of an alerting system 200. The system 200 may include a data extractor 202 and contact management system 206 that are added to an existing EMR system so as to provide alerting functionality. The existing system, before the addition of the alerting system 200, may include a variety of institutional databases 208 that may take a variety of forms, and may be used by a healthcare institution in its ordinary course of business. Such databases could range from EMR databases of various types, databases that track contact information for caregivers who are employed by a system, accounting databases, and databases used to assist caregivers with making diagnoses (e.g., expert systems). The system 200 may also include a data warehouse 204, which may be provided with read access to various portions of the institutional databases 208 and may be employed to extract information from the institutional databases 208 and reformat and store the data where it can be queried and otherwise manipulated more readily by components such as the data extractor 202.

While described here as an addition to an existing healthcare computing system, the alerting system 200 may also be implemented at the same time as the main system. However, various advantages may be obtained by implementing the alerting system 200 as a distinct module from other subsystems that are part of the main system, including by installing the alerting system 200 on a separate server system, with hooks to the alerting system 200 in modules for other portions of a healthcare information system.

The data extractor 202 may be triggered by an internal clock on a periodic basis to extract data from the data warehouse 204, where the relevant data—in this example—relates to conditions of patients in a healthcare system who are currently connected to bed-side monitors. Several particular pieces of data are gathered in one example relating to sepsis monitoring. First, information from laboratory reports on the patient's white blood cell count, lactate, base, and anion gap may be retrieved and identified. Such information may be indicative of a hypotension or organ hypo perfusion. Second, the EMR system may be queried for any culture order in a determined previous time period, such as a prior 96-hour time period. Such orders may represent a suspicion, by a caregiver, that the patient is suffering from infection. Third, the EMR system and/or the bed-side monitor may be queried for information about patient temperature, heart rate, and respiration rate, and also patient white blood cell count (e.g., via block 210). Such information may indicate a problematic systematic inflammatory response by the patient, in response to infection. The alert system may then combine the various access information according to a formula to generate a "score" for the patient, where an alert is generated if a predetermined score is exceeded. Additional information may be taken into account in determining the score or in determining whether the score should trigger an alert, including the weight, age, and general physical condition of the patient, and other problems that the patient may have (e.g., heart disease or other conditions that could lower the patient's ability to fight infection).

Notes in the EMR may also be parsed and analyzed. For example, the system may identify terms in the notes such as "sepsis," "inflammation," "infection," and the like, as clues to the caregivers' beliefs that there may be a sepsis-related problem for the patient.

Rules may also be applied across multiple readings to ensure that transient conditions of the patient do not generate a false positive or a false negative. For example, the alert system may ensure that heart rate, respiratory rate, and blood pressure exceed threshold values across four consecutive readings. Moreover, rules may be used to suppress alerts in appropriate circumstances. For example, alerts may be suppressed for a predetermined period, such as 14 days, after evidence shows that the patient has been attended to for sepsis, under the assumption that the care giving team will know about the problem, continue to be treating it, and may lose faith in the system if the system provides unnecessary alerts.

The querying of the EMR system in these examples may be in real-time or in batch mode. For example, a query to the EMR system may be performed for each patient by an alerting system. Alternatively, all relevant patient data may be pulled periodically from the EMR system to a separate data storage system (e.g., the data warehouse 204) local to the alerting system, and the alerting system may then access the data directly from there, so as to better balance the loads that may be placed on the EMR system.

If the data extractor 202 makes a determination that a potentially dangerous condition exists, it may check the patient's EMR in the various manners discussed above to determine whether the patient is already being treated for sepsis. If the patient is being treated, the system may continue to monitor the patient, but need not send out an alert. If the patient is being treated in an ambiguous manner—so that it is possible that the caregiving team recognizes the sepsis condition and it is possible that they do not—a lesser level of alert may be sent, such as by a note being placed automatically in the patient's EMR or a non-urgent message being sent to an appropriate caregiver (e.g., a shift nurse).

If an alert is appropriate, the system may send a signal to the contact management system 206, which may be a system that prepares and routes a variety of messages to mobile devices 216 of caregivers in the system 200. Such preparation and routing, in this example, may include an initial determination by the system 200, of which caregiver is currently responsible for the patient, such as an on-call physician or nurse assigned to an ICU where the patient is stationed. The preparation of the message may further include the generation of a message whose text indicates an identity of the patient, either directly (by name) or indirectly (by location in the ICU) and the nature of the condition that triggered the notification. The contact management system may further query the institutional databases 208 such as to find contact information (e.g., an email address) for caregivers.

In certain circumstances, the generation of an alerting message may be blocked or delayed. Typically, such action may occur to prevent the generation of false positive reports that would result in caregivers having less respect for the system 200, and in the quality of care for patients declining. For example, the system 200 may require that an alerting condition be present for a certain number of cycles of the system 200, such as over a period of several hours or measurement cycles. Also, the system 200 may limit the number of notifications that a particular caregiver receives, so that the caregiver is not being bombarded with notifications about a particular patient, and is rendered unable to determine which are serious and which are not.

The alert message that is provided to a caregiver may be "rich", in that it may permit interaction by the alerted caregiver in order to obtain additional information about the patient and the patient's condition automatically. For example, the message may include one or more hyperlinks that aim back to the patient's EMR (which can be exposed after the caregiver provides adequate ID and password) so that the caregiver can obtain full access to the patient's EMR and thus can make a remote determination about how best to handle the event. For example, a physician at home may determine that the best immediate route is to have an on-site caregiver enter the patient's room and directly monitor the patient. The physician may then talk to the on-site caregiver, including by video link or transmitted photos (e.g., from physician smartphone to nurse smartphone or tablet PC) to obtain additional information that may not have been otherwise accessible to the physician.

The system 200 may, after providing the alert, wait a predetermined time period, whose duration can depend on the severity of the sepsis condition as determined by the various gathered information identified above, before checking the patient's data again. Such a check may be of updated patient status information to determine whether the patient's status has improved since the alert was generated (e.g., better blood pressure, heart rate, and respiratory rate). The check may also be for entries in the patient's EMR after the time of the alert so as to determine whether responsive care has been given to the patient. If the system 200 determines that there is a problem in either situation, it may send another alert, either to the initially-alerted caregiver or to another caregiver. Such an alerting process may continue until the system 200 has seen evidence that the patient's problem has been adequately addressed.

In this manner, the system 200 can automatically identify potential dangerous conditions for a patient even if no caregiver has yet to make a determination that the patient has a sepsis problem. The system 200 can also generate an alert that is custom, in that it can be transmitted remotely to a caregiver using whatever messaging technology the caregiver prefers (e.g., smart phone, text pager, etc.) and can give information about the nature of the alert. In addition, it can manage the number and type of message that is delivered so that the overall operation of system 200 is not overly intrusive to caregivers. Moreover, the system 200 may ensure, separately from explicit reporting by caregivers, that the patient's needs have been addressed. As a result, the care of a patient may be improved.

Figure 2B:
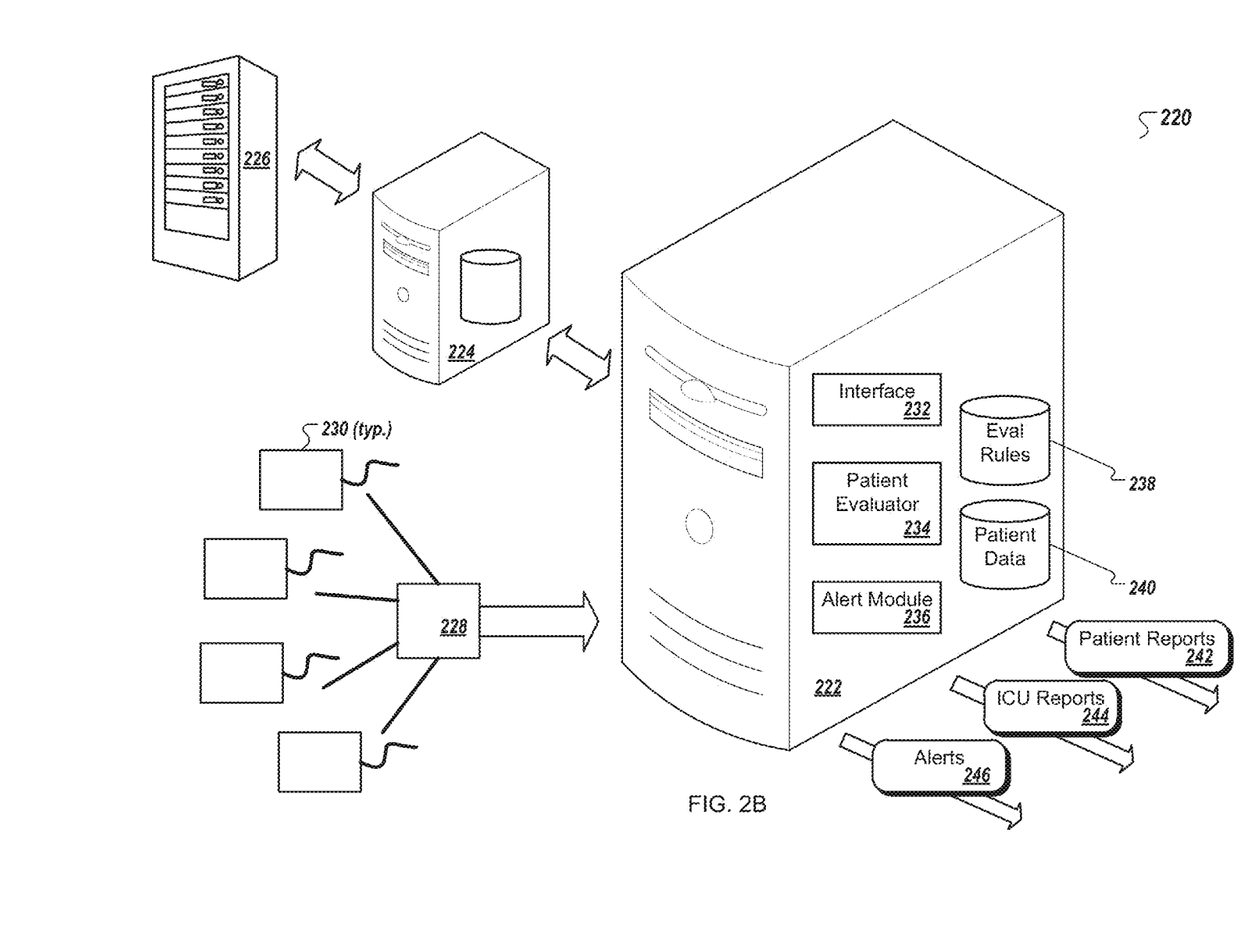
FIG. 2B is a schematic diagram of a computer system for alerting caregivers about sepsis problems with patients in a healthcare facility.

FIG. 2B is a schematic diagram of a computer system 220 for alerting caregivers about sepsis problems or similar problems with patients in a healthcare facility. In general, the system 220 may comprise all or a portion of system 200 in certain implementations—though more detail is shown for certain portions of system 220

The system 220 generally includes an alerting computer system 222 which may be made up of one or more computer servers programmed with computer code to analyze various scattered data in a healthcare system so as to generate an alert that a dangerous condition may exist for one or more patients who are using bed-side monitors in the system 220. The computer system 222 may capture its data from a number of bed-side monitors 230 via a data aggregation unit 228. The unit 228 may include a database that stores and manages various parameters concerning bed-side monitors that are operating in one or more ICU's in a healthcare system, including bed-side monitor set points and readings (e.g., respiration rate, heart rate, oxygen content, etc.) taken by the various bed-side monitors. The unit 228 may also include an interface that operates according to a known API so that data about the bed-side monitors 230 can be communicated to the computer system 222 in a predefined manner.

The computer system 222 may also gather data from a data warehouse 224, which may take a variety of forms, and is generally designed to be a centralized location where data about a healthcare system may be easily accessed and manipulated. The warehouse 224 may in turn query a data system 226 for the entire healthcare system. The data system 226 is shown here as a rack of servers to indicate that the data system 226 will typically involve a number of different servers scattered across a campus or larger network of healthcare facilities, though the particular physical form of any of the computer systems or sub-systems shown here is not critical and can take any appropriate form. Also, where the term server is used, the system may implement the relevant functionality in a portion of a server (e.g., a virtual machine), a single dedicated servers, or multiple servers.

The system 222 includes a variety of components that allow it to obtain data relating to bed-side monitoring of patients and to generate alerts in appropriate circumstances. Although the receipt of information from the bed-side monitors 230 is shown here as being direct, such information could also be obtained through an EMR system.

An interface 232 is provided so that system 222 can query unit 228, data warehouse 224, and other appropriate data stores to obtain information that can be used to determine the condition of a patient or patients. Such data may be used by a patient evaluator 234, in combination with patient evaluation rules 238 that are stored by the system 222, to determine whether a patient could be in a potentially dangerous condition. Patient data 240 may also be stored and used by the patient evaluator 234, such as identification information for the patient, the ICU in which they are staying, etc. Example rules are discussed above and below in more detail.

An alert module 236 may be notified by the patient evaluator 234 when a potentially dangerous condition is determined to exist. The alert module may then gather information about the patient, and the alerting condition, may make a determination about whether a likely problem exists, and may prepare a message (box 246) to be sent to an appropriate caregiver.

The system 222 may also generate information in addition to individual alerts. For example, patient reports may be generated for administrators who query the system 222, and such reports may indicate the number of times an alert has been generated for a particular patient and the nature of the alerts. Such a query may be made by an administrator trying to determine whether alerts have been acted on appropriately, or by a caregiver from the patient's room, to determine how long an alerting condition has existing, in determining a proper remedial plan of care for the patient. Also, more general ICU reports may be generated, and may show an administrator a compilation of alert activity for one or more ICU's, which may assist the administrator in staffing caregivers or determining whether appropriate ICU care is being provided. The reports may be persistent, in that they are generated automatically, such as being generated each day for an arriving shift nurse. The reports may also be triggered manually, such as by a supervising physician who wants to see an overview of alerting activity for a patient, a ward, or an entire system.

Figure 3:
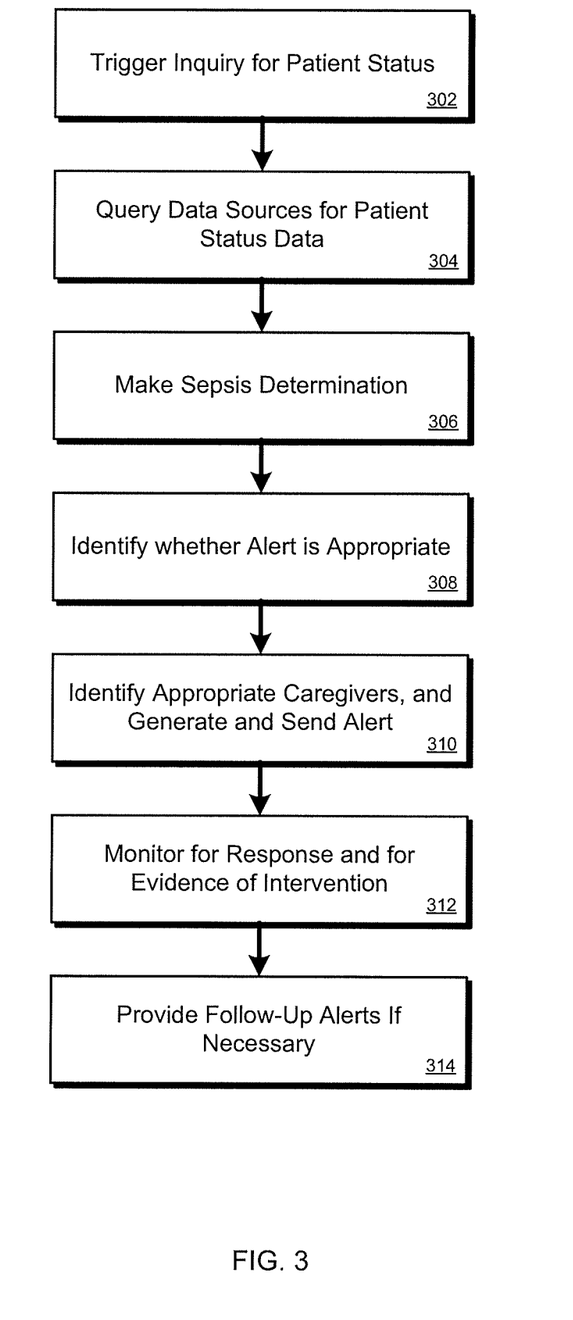
FIG. 3 is a flow chart of a process for monitoring a patient for sepsis problems and alerting caregivers if problems are identified.

FIG. 3 is a flow chart of a process for monitoring a patient for sepsis problems and alerting caregivers if problems are identified. The process begins at box 302 where an inquiry for patient status is trigger. The triggering may occur on a periodic basis for all patients who are currently active in the system, or only patients flagged as having a certain status, such as ICU patients. The timing of the inquiries may be varied so that different patients are addressed at different times, and a load manager may be employed to smooth out the load on the system of making the inquiries.

At box 304, data sources are queried for patient status information. Such querying may occur as described above, and may including querying of an EMR record for the patient to obtain various measured and test data for the patient. The query may also obtain real time status data for the patient, such as heart rate, respiratory rate, and blood pressure, either by querying an EMR system that collects such information or by querying bed-side monitors of a patient directly.

At box 306, a sepsis determination is made. The determination may be made according to an algorithm that takes into effect the various measured variables and provides appropriate weights to each. The particular weights and variables may be determined readily by appropriate study of a patient population, and actual diagnoses by physicians of patients in the population. Particular factors may be broken into 4 domains as follows:

"Domain 1" (measured within a prior 72 hour window). This domain includes inspection to identify any microbiology culture order, which may indicate a suspicion by a caregiver that the patient has an infection.

"Domain 2" (measured within a prior 24 hour window). This domain would be triggered by two or more of the following: respiratory rate>25 breaths/min; heart rate>90 beats/min; white Blood Cells>12000 cells/$mm^3$; white Blood Cells<4000 cells/$mm^3$; body temperature>38.6 C; Body temperature<36.0 C. Such factor may indicate systematic inflammatory response.

"Domain 3" (measured within a prior 24 hour window). This domain would be triggered by any one of the following: mean arterial Blood Pressure<65 mm Hg or systolic blood pressure<90, lactate>2.5 mmol/l; base<−5 mmol/l; anion gap>12 mEq/L. Such factors may indicate hypotension or organ hypo perfusion.

"Domain 4" is additional rules that a design of a system may want to impose, based on experience with an ICU program and/or an automatic alerting system. For example, rules may impose that heart rate, mean arterial blood pressure, and respiratory rate should exceed threshold level for 3 consecutive readings before an alert is generated. Also, a rule may be imposed so that the same patient case is not alerted in 14 days. The syntaxes for certain rules may be pre-programmed into a system also, and a user may be allowed to select which rules to apply and triggering values for those rules. For example, a user could change the numbers 3 and 14 in the prior two rules, so as to fine-tune the rules to the needs of a particular organization.

Under a "failure of rescue" concept, rules may identify a detection of a provider action or inaction that is to be triggered only if the provider has not followed up with early goal directed therapy. For example, detection of central venous pressure (CVP) can be a sign to the system that providers were aware of such a patient condition. Missing this data point is a "failure to rescue" event that triggers an alert.

At box 308, the process determines whether an alert is appropriate. For example, according to the rule just mentioned, the system may determine that the patient is in severe sepsis, but EMR data may indicate that the care giving team is already well-aware of that fact and is dealing with it. As described above, such a determination can be made by recognizing in the EMR data that a sepsis team has been alerted, that the patient has recently been given a central line, or via other actions by the caregiving team that are consistent with a sepsis treatment course of action. In such a situation, an alert would be unnecessary and potentially annoying.

At box 310, appropriate caregivers are identified, and an alert or alerts are generated and sent. The appropriate caregiver may be determined by querying a hospital information system to identify the location of the patient and the caregiver currently responsible for that location. Also, contact records in the system may be queried so as to obtain a page number, email address, or other appropriate contact information for the caregiver.

At box 312, the process monitors for a response form the caregiver. For example, the caregiver may be asked to confirm that they received the alert, and if such confirmation is not received within a predetermined time period (e.g., several minutes), a separate message may be sent to another, back-up caregiver.

At box 314, follow-up alerts are provided if necessary. As discussed above, the EMR data may be monitored for positive evidence that the alerting condition is being address by the care giving team. If such evidence does not appear within a predetermined time period, the process may return back to generating more alerts, either to the caregivers who were initially alerted or to others in an organizations.

A study of particular patients in ICUs was conducted in particular settings, as next described, in order to determine whether intelligent evaluations of patient condition could be made automatically according to particular predetermined rules.

Example

An "sepsis sniffer" automatic screening tool like the systems described above was applied to a three-month data set of patients' data from electronic medical records in a medical intensive care unit. In the study, 50 of 401 consecutive patients developed severe sepsis/septic shock during an ICU stay. The sniffer demonstrated a sensitivity of 86%, specificity 83%, and positive predictive value 43%.

In the studied system, a Microsoft SQL-based integrative database, "Intensive Care Unit (ICU) data mart", accumulated data within one hour from its entry into the electronic medical records and served as the main data source for rules development. Severe sepsis and septic shock were defined according to standard consensus conference criteria. These criteria included blood culture order within 72 hours AND (two of (respiratory rate above 25 OR WBC above 12000 OR temperature below 36.0 C) and (heart rate above 90 OR WBC below 4000 OR temperature above 38.6 C)) AND hypotension or organ hypo perfusion as indicated by (mean arterial blood pressure below 65 OR lactate above 2.5) or (metabolic acidosis base less than −5 OR anion gap greater than 12).

The data set was retrospectively continuously scanned with an electronic alert based on severe sepsis/septic shock criteria ("sniffer").

Results. From 401 consecutive admissions to the medical ICU during 90 days study period (August-October 2007). Two critical care experts blinded to the sniffer results diagnosed 50 severe sepsis/septic shock cases. The screening engine sent a total of 101 alerts and correctly identified 43 patients with the syndrome.

EMR screening algorithm based on the consensus conference for severe sepsis/septic shock criteria had a sensitivity of 86% (95% CI 73-94) and a specificity of 83% (95% CI 78-87). Positive and negative likelihood ratios for diagnosis of severe sepsis/septic shock were 5.01 (95% CI 3.87-6.50) and 0.17 (95% CI 0.08-0.34). Electronic alert had a positive predictive value of 43% (95% CI 33-52) and negative predictive value 98% (95% CI 95-99).

Conclusions. In this study we demonstrated the feasibility of near-real time computerized screening of EMRs for early diagnosis of severe sepsis/septic shock syndrome (sepsis "sniffer"). The sniffer based on standard consensus conference criteria demonstrated adequate positive predictive.

Figure 4:
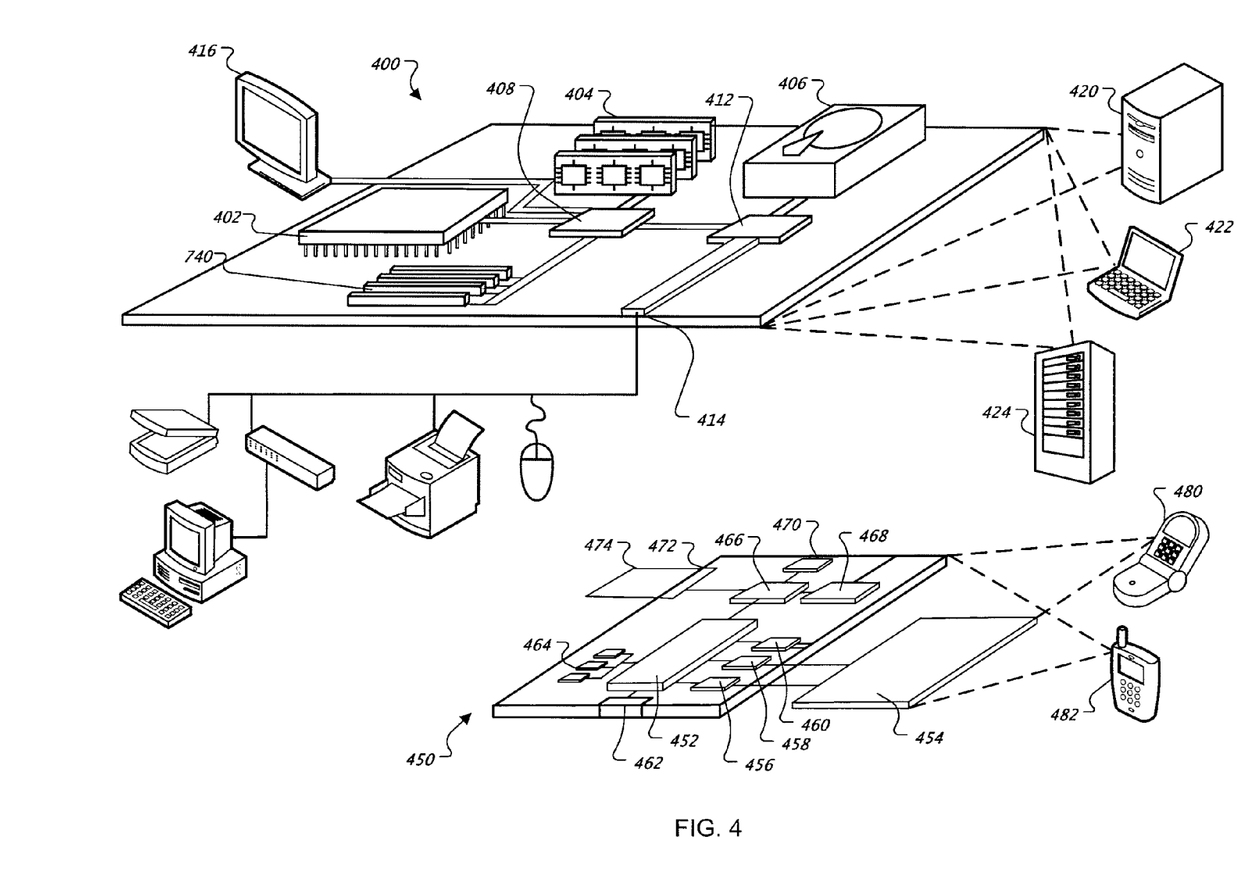
FIG. 4 shows an example of a generic computer device and a generic mobile computer device, which may be used with the techniques described here.

FIG. 4 shows an example of a generic computer device 400 and a generic mobile computer device 450, which may be used with the techniques described here. In particular, computer device 400 may be used in the various servers identified above, and mobile computer device 450 may be used by caregivers in receiving and responding to alerts. Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 400. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 404, the storage device 406, memory on processor 402, or a propagated signal.

The high speed controller 408 manages bandwidth-intensive operations for the computing device 400, while the low speed controller 412 manages lower bandwidth-intensive operations. Such allocation of functions is exemplary only. In one implementation, the high-speed controller 408 is coupled to memory 404, display 416 (e.g., through a graphics processor or accelerator), and to high-speed expansion ports 410, which may accept various expansion cards (not shown). In the implementation, low-speed controller 412 is coupled to storage device 406 and low-speed expansion port 414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a microdrive or other device, to provide additional storage. Each of the components 450, 452, 464, 454, 466, and 468, are interconnected using various buses, and several of the components may be mounted on a common motherboard or in other manners as appropriate.

The processor 452 can execute instructions within the computing device 450, including instructions stored in the memory 464. The processor may be implemented as a chipset of chips that include separate and multiple analog and digital processors. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT LCD (Thin-Film-Transistor Liquid Crystal Display) or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provide in communication with processor 452, so as to enable near area communication of device 450 with other devices. External interface 462 may provide, for example, for wired communication in some implementations, or for wireless communication in other implementations, and multiple interfaces may also be used.

The memory 464 stores information within the computing device 450. The memory 464 can be implemented as one or more of a computer-readable medium or media, a volatile memory unit or units, or a non-volatile memory unit or units. Expansion memory 474 may also be provided and connected to device 450 through expansion interface 472, which may include, for example, a SIMM (Single In Line Memory Module) card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provide as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, memory on processor 452, or a propagated signal that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS (Global Positioning System) receiver module 470 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented sepsis alerting method, comprising:
   automatically extracting with a computer system, from records maintained for a patient under care in a healthcare facility, information from an electronic medical record;
   obtaining with the computer system information about real-time status of the patient;
   using the information from the electronic medical record and the information about the real-time status to determine whether the patient is likely to be suffering from dangerous probability of sepsis;
   electronically alerting an initial caregiver over a network if it is determined that a potentially dangerous level of sepsis exists;
   using information from the electronic medical record, after a determined time period relating to a time when the initial caregiver was alerted, to determine whether treatment for sepsis is already being provided to the patient and whether a potentially dangerous level of sepsis continues to exist; and
   electronically alerting a follow-up caregiver over a network if it is determined that a potentially dangerous level of sepsis exists and that treatment for sepsis is not already being provided.

2. The method of claim 1, wherein the follow-up caregiver is different than the initial caregiver.

3. The method of claim 1, wherein obtaining real-time status of the patient comprises querying, with the computer system, a bed-side monitor for the patient or a controller to which the bed-side monitor reports information about the patient.

4. The method of claim 1, wherein determining whether the patient is likely to be suffering from sepsis comprises applying predetermined rules to values of patient parameters obtained with the computer system.

5. The method of claim 4, wherein the values include values for patient heart rate, respiration rate, and blood pressure.

6. The method of claim 4, wherein the values include values generated by a blood test on the patient's blood.

7. The method of claim 4, wherein the values include keywords in notes in an electronic medical record for the patient.

8. A non-transitory machine-readable tangible medium having recorded and stored thereon instructions that when executed on one or more electronic computers, perform actions comprising:
   automatically extracting with a computer system, from records maintained for a patient under care in a healthcare facility, information from an electronic medical record;
   obtaining with the computer system information about real-time status of the patient;
   using the information from the electronic medical record and the information about the real-time status to determine whether the patient is likely to be suffering from dangerous probability of sepsis;
   using information from the electronic medical record to determine whether treatment for sepsis is already being provided to the patient; and electronically alerting a caregiver over a network if it is determined that a potentially dangerous level of sepsis exists and to provide a follow-up alert over the network if it is determined that a potentially dangerous level of sepsis continues to exist and that treatment for sepsis has not been provided to the patient in a determined time period.

9. The machine-readable tangible medium of claim 8, wherein the actions further comprise:

electronically automatically monitoring with the computer system the patient's electronic medical record to determine whether intervention has occurred to treat the potentially dangerous level of sepsis; and providing follow-up electronic alerts if a determination is made that intervention has not occurred.

10. The machine-readable tangible medium of claim 8, wherein obtaining real-time status of the patient comprises querying, with the computer system, a bed-side monitor for the patient or a controller to which the bed-side monitor reports information about the patient.

11. The machine-readable tangible medium of claim 8, wherein determining whether the patient is likely to be suffering from sepsis comprises applying predetermined rules to values of patient parameters obtained with the computer system.

12. The machine-readable tangible medium of claim 11, wherein the values include values for patient heart rate, respiration rate, and blood pressure.

13. The machine-readable tangible medium of claim 11, wherein the values include values generated by a blood test on the patient's blood.

14. The machine-readable tangible medium of claim 11, wherein the values include keywords in notes in an electronic medical record for the patient.

15. A computer-implemented system to monitor and report on patient condition, the system comprising:

a computer system that implements a data extractor to automatically extract, from records maintained for a patient under care in a healthcare facility, information from an electronic medical record and obtain information about real-time status of the patient;

a patient evaluator programmed to using information extracted by the data extractor to determine whether the patient is likely to be suffering from dangerous probability of sepsis, and to determine whether treatment for sepsis has been provided to the patient; and a contact management system arranged to electronically alert a caregiver over a network if the patient evaluator determines that a potentially dangerous level of sepsis exists, and to provide a follow-up alert over the network if the patient evaluator determines that a potentially dangerous level of sepsis continues to exist and that treatment for sepsis has not been provided to the patient in a determined time period.

16. The system of claim 15, further comprising an alerting system to determine whether the patient is already receiving treatment for sepsis and to prevent the contact management system from generating an electronic alert if the patient is already receiving treatment for sepsis.

17. The system of claim 15, further comprising an alerting system to automatically monitor the patient's electronic medical record to determine whether intervention has occurred to treat the potentially dangerous level of sepsis and to initiate follow-up electronic alerts if a determination is made that intervention has not occurred.

* * * * *